United States Patent [19]

de Medinaceli

[11] 4,306,561

[45] Dec. 22, 1981

[54] HOLDING APPARATUS FOR REPAIRING SEVERED NERVES AND METHOD OF USING THE SAME

[75] Inventor: Luis de Medinaceli, Bridgeport, Conn.

[73] Assignee: Ocean Trading Co., Ltd., Grand Turk, Turks and Caicos Isls.

[21] Appl. No.: 91,541

[22] Filed: Nov. 5, 1979

[51] Int. Cl.³ .............................................. A61B 17/36
[52] U.S. Cl. ........................... 128/303.13; 128/303.1; 128/334 C
[58] Field of Search .............. 128/334 R, 334 C, 346, 128/325, 321, 322, 326, 303.1, 335, 303.13; 24/81 AD

[56] References Cited

U.S. PATENT DOCUMENTS 3,561,448  2/1971  Peternel ......................... 128/346 X
3,833,002  9/1974  Palma ............................. 128/346 X

FOREIGN PATENT DOCUMENTS 749707  1/1967  Canada ............................ 128/334 R

*Primary Examiner*—Michael H. Thaler
*Attorney, Agent, or Firm*—Mattern, Ware, Davis and Stoltz

[57] ABSTRACT

By circumferentially embracing both the proximal and distal portions of a severed nerve at positions removed from the severed ends and controllably moving the severed portions into abutting, juxtaposed contacting relationship, the reattachment and repair of severed nerves is achieved. Preferably, both portions of the severed nerve are embraced within a holding member which incorporates nerve securing means at the desired location. In addition, the preferred nerve holding member incorporates nerve cooling components, electrical pulse stimulation means for directing a pulse from the proximal portion towards the distal portion, and temperature sensing components for monitoring the temperature of the nerve.

6 Claims, 10 Drawing Figures

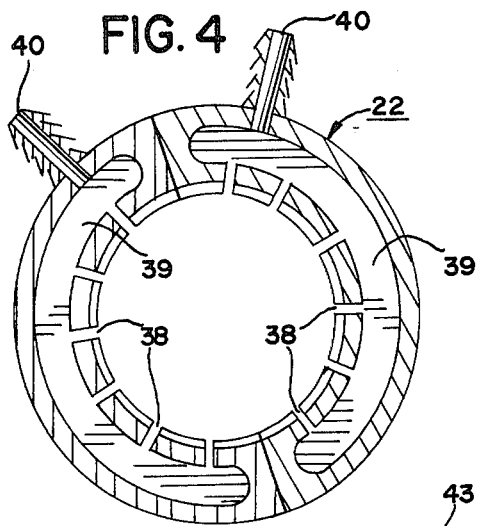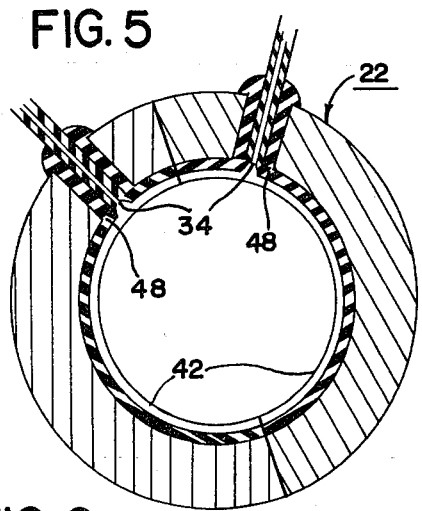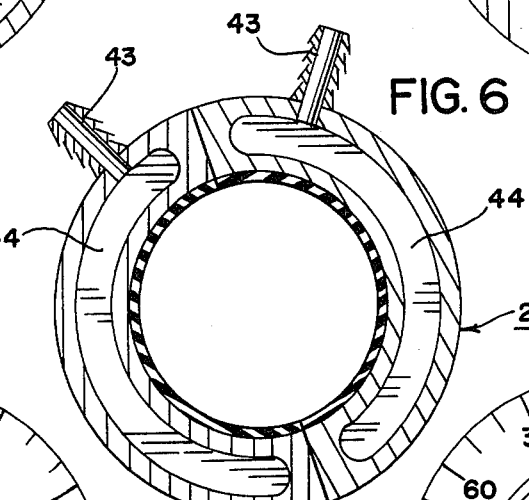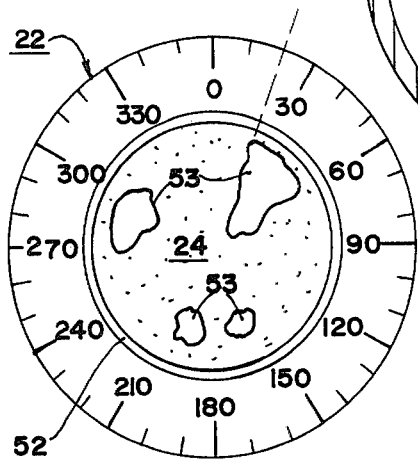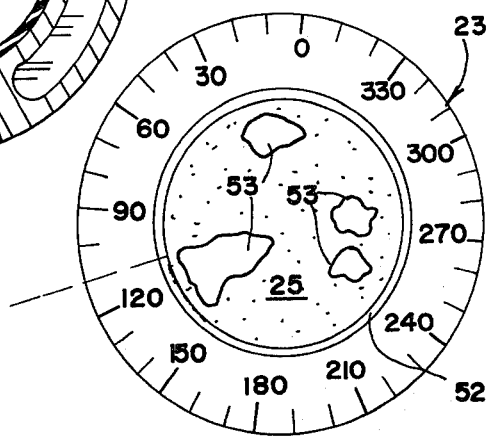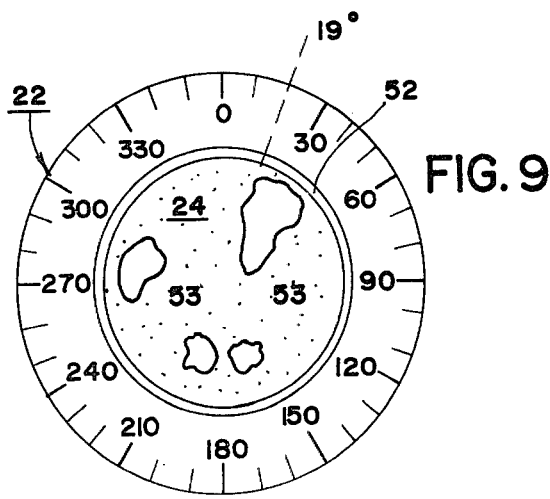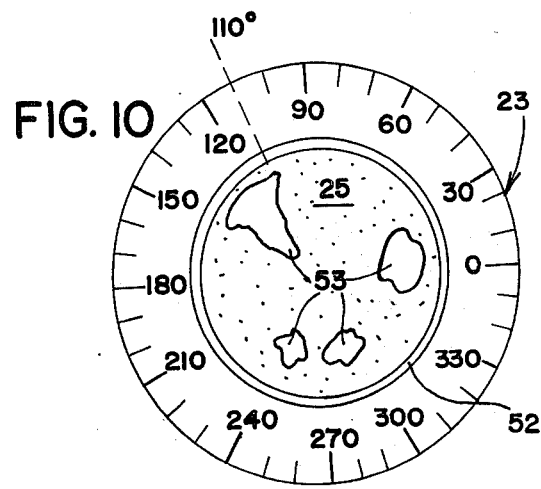

HOLDING APPARATUS FOR REPAIRING SEVERED NERVES AND METHOD OF USING THE SAME

TECHNICAL FIELD

This invention relates to methods and apparatus for reattaching and repairing severed nerves, rejoining the severed distal end to the proximal end, and achieving substantial restoration of function.

BACKGROUND ART

Although numerous attempts have been mde to reattach and repair transected nerve fibers, all such methods have failed. For the last century, up until the time of the present invention, all attempts to repair transected nerve fibers, so that the previously transected nerve fiber allows the passage of nervous impulses, have been unsuccessful.

One of the main reasons for the failure of the prior art methods and apparatus to repair transected nerves is the tendency to apply traditional surgical techniques to the nerve fibers. Although these traditional surgical techniques have proven completely effective with tissues, these techniques fail when applied to an injured nerve. One of the basic reasons for inapplicability of traditional surgical techniques to nerve fibers is the fact that each neuron comprises a single cell extending from the cortex of the brain through the spinal cord to the particular extremity in which the nerve fiber is found. Since the neuron comprises only a single cell from one end to the other, traditional techniques relating to tissues which comprise a group of cells have proven to be totally inapplicable.

The present inability to repair transected nerves is becoming increasingly important when the advances in microsurgical repair of tissue are considered. Using advances in micro-surgery, severed arms and legs may now be fully reattached without rejection by the body defense mechanisms. However, in spite of these surgical advances, control over muscles contained within the previously severed limb are virtually totally lost, since present day surgical techniques are unable successfully to repair the severed nerves in order to allow the nervous impulses to be carried to the extremities.

In general, prior art techniques to repair severed nerves have failed due either to an attempt to draw the nerve ends together by the nerve end's epineurium sheath or by attempting to draw the entire nerve ends into juxtaposition using vacuum. Both of these methods have failed due to the structure and physical characteristics of the nerve.

In particular, when a nerve end is drawn endwise by its epineurium, the fascicles of bundles of nerve fibers contained within the epineurium withdraw from the severed end, like an arm pulling up inside a sleeve. As a result, when the epineuria on facing nerve ends are joined by suturing, repair is not realized since the fascicles of the nerve fibers have withdrawn away from the connected zone and are not reattached.

In an attempt to resolve this problem, the vacuum technique was developed. However, the drawing of the nerve ends towards each other using vacuum merely causes the protoplasm forming the nerve fibers to be sucked out into the vacuum line. As a result, successful repair is not realized.

These prior art techniques are exemplified in the following patents:

William E. Kuhn's U.S. Pat. Nos. 3,960,151 and 3,916,905 relate to open-ended tubes into which the respective severed ends of a sectioned nerve are drawn by a partial vacuum.

James R. Palma's U.S. Pat. Nos. 3,786,817 and 3,833,002 likewise show tubes having open ends into which the ends of the sectioned nerve are drawn in juxtaposition by vacuum.

Michael B. Collito's U.S. Pat. Nos. 3,254,650 and 3,316,914 show "plumbing union" type flanges for severed blood vessel ends which may be everted and secured to the flanges and then clamped in position for suturing or healing.

Anastomotic couplings are shown in Sparks U.S. Pat. No. 3,357,432, Zack U.S. Pat. No. 2,453,056 and Hardy U.S. Pat. No. 3,974,835, and a surgical clamp which squashes blood vessels flat for anastomosis is shown in Pearson's U.S. Pat. No. 2,796,867.

Therefore, it is a principal object of this invention to provide methods and apparatus which allows both portions of a severed nerve to be held and moved into endwise juxtaposition without disturbing the fascicles of the nerve.

Another object of the present invention is to provide methods and apparatus for repairing severed nerves which allow the nerves to be preserved prior to the repair procedure without degradation or degeneration of the nerve.

Another object of the present invention is to provide nerve holding means which incorporate in single unitary structures all necessary provisions for successfully repairing and reconnecting severed nerves.

Another object of the present invention is to provide a method and apparatus for repairing severed nerves wherein the severed nerve ends can be held in juxtaposed contacting relationship for several hours and can then be quickly and easily removed from the holding apparatus.

A further object of the present invention is to provide a method and apparatus for repairing severed nerves wherein the ends of the severed nerve can be optically viewed and adjusted in order to maximize reattachment of matched fascicles.

Other and more specific objects will in part be obvious and will in part appear hereinafter.

DISCLOSURE OF THE INVENTION

Using the revolutionary teaching of the present invention, severed nerve fibers can now be successfully reattached and repaired in order to allow the transmission of active potentials immediately after the transection has been restored. One feature of the present invention which is of particular importance in the success of these reattachment and repair procedures is separately holding both the distal portion and the proximal portion of the severed nerve at points spaced away from the transection. In this way, both the epineurium or surrounding sheath of the nerve ends, and the fascicles contained within the epineurium, are simultaneously secured for unitary movement. As a result, withdrawal of the fascicles from the nerve ending is eliminated as well as loss of the nerve protoplasm.

Another aspect of the present invention is to provide a separate nerve holding chamber through which cooling fluid is circulated in order to reduce the deterioration of the nerve prior to its reattachment and repair.

Using the cooling chamber in accordance with the present invention, a nerve can be maintained for several hours, while other surgical procedures are progressing, without any detrimental loss of the nerve. In addition, electrical stimulation means are provided, preferably as a portion of the holding chamber, with the electrical pulse stimulation having the capability of being repeatedly and continuously applied for several hours in order to assist in the reattachment and repair process.

In the preferred construction, a single quickly removable chamber incorporates nerve holding means, cooling chambers, and means for electrical stimulation. In this way, a single chamber is quickly and easily attached to the proximal end of a nerve with a second chamber being attached to the distal end of the nerve in order to provide the requisite holding support, preservation, and healing capabilities for reattachment and repair of the severed nerve.

Another important aspect of the present invention is the preferred trimming of the proximal nerve end prior to bringing the distal end into juxtaposition therewith. It has been found that after transection of the nerve, the proximal end is capable of healing and growing again. Although the biological mechanism is not fully understood, it appears that the proximal portion of the nerve forms a healing membrane at the severed end thereof in order to retain its protoplasm.

Since the mere reattachment of the open distal end to the healed, closed proximal end of the severed nerve would not provide any reattachment and repair, it is important that the proximal end of the severed nerve be trimmed in order to reopen the proximal end of the nerve. Only in this way will the transmission of nervous impulses from the proximal portion to the distal portion be achieved.

Further, the matching alignment of the trimmed proximal nerve end with the juxtaposed distal nerve end may be performed by visual observation, which may be enhanced by microscopic or fiber optic systems or computer evaluation and matching of the severed fascicle end images.

The invention accordingly comprises the several steps and relation of one or more of such steps with respect to each of the others and the apparatus embodying features of construction, combination of elements and arrangements of parts which are adapted to affect such steps, all as exemplified in the following detailed disclosure and the scope of the invention will be indicated in the claims.

THE DRAWINGS

For a fuller understanding of the nature and objects of the invention, reference should be had to the following detailed description taken in connection with the accompanying drawings, in which:

FIG. 4 is a cross sectional end view of the chamber of the present invention taken along line 4—4 of FIG. 3;

FIG. 5 is a cross sectional end view of the chamber of the present invention taken along line 5—5 of FIG. 3;

FIG. 6 is a cross sectional end view of the chamber of the present invention taken along line 6—6 of FIG. 3;

FIG. 7 is an end view of the chamber of the present invention, taken along line 7—7 of FIG. 3;

FIG. 8 is an end view of a second cooperating chamber attached to the other end of the severed nerve, taken along line 8—8 of FIG. 3 and shown before rotational alignment;

Figure 1:
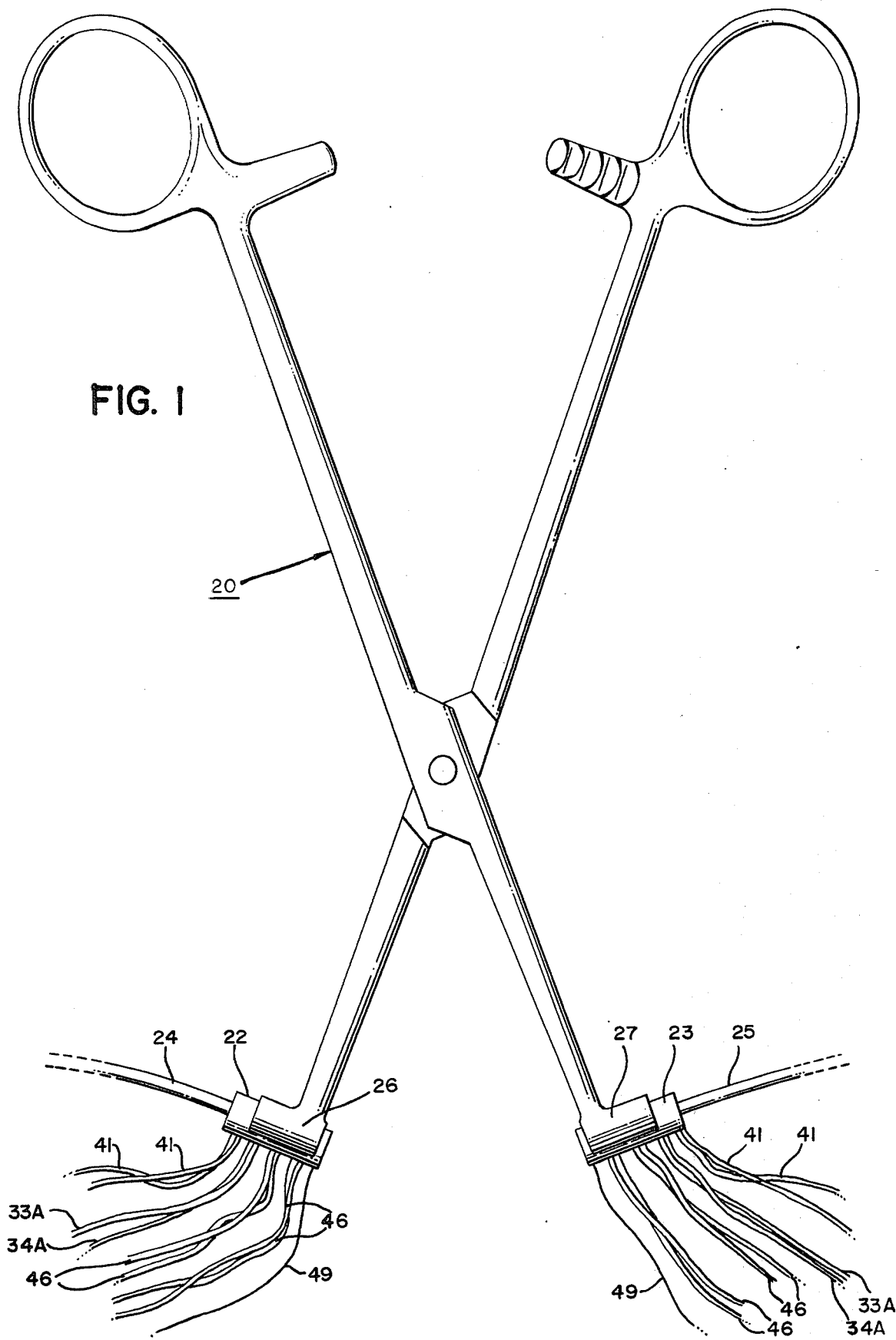
FIG. 1 is a diagrammatic top plan view of a simple holding and clamping arrangement whereby the nerve end holding chambers of the present invention are securely held in the open position ready for viewing.

FIG. 9 is an end view of the chamber of the present invention substantially identical to the view of FIG. 7, positioned for comparison, and FIG. 10, is an end view of the second chamber of the present invention attached to the second portion of the severed nerve substantially identical to the view of FIG. 8 but shown rotated through an angular arc for maximizing the juxtaposition of identical fascicles and axons for optimum repair.

BEST MODE FOR CARRYING OUT THE INVENTION

Using the prior art techniques, a patient must wait at least six months, and sometimes up to 1½ years after the surgical reattachment of the severed limb before knowing if the severed nerves have grown back. However, by employing the method and apparatus of the present invention, reattachment and repair of the severed nerve is now obtainable with transmission of action potentials or nerve impulses being immediately restored after recombination of the severed nerve.

It has long been known that when an amoeba is cut in two, the part which includes the nucleus survives, while the other portion wastes away. The situation is the same when a neuron is sectioned, since its proximal part survives, while the distal end undergoes the Wallerian degeneration. There is then a striking contrast between the inability to repair that injured axon and the inability to provent the extraordinary growth of the proximal portion, growth which culminates in the production of sometimes unbearable neuromes.

If the proximal portion of the sectioned neuron survives, it means that the cell is able to close itself again after the lesion by solidifying its protoplasm and building up a new membrane from this protoplasm. This healing phenomenon is well known. It must occur and be completed over a rather short period of time. Thus any effort to suture the extremities of a previously sectioned nerve should fail, since in the best cases this would only put together two groups of cellular extremities, the half of which is healed, closed upon itself, the other half being therefore excluded.

The first rule of surgery of the anon should thus be to "open " again that already healed cell, so that it becomes possible to "graft" or "re-implant" the portion that has been cut off. Once the cell has been freshly opened again, some time is needed to properly juxtapose the extremities of the axon. It is compulsory to slow down the cellular metabolism during that time without of course damaging the nerve. Cold seems to be the most efficient agent. Moderate cold must be used so as not to destroy the cell by frost. The temperature which can be expected to be the best ranges between +4° C. and +9° C.

The problem is not primarily at the proximal end of the nerve which is capable of healing and then of growing again. The severity of the lesion is greatest at the distal end, which when left alone degenerates. Whatever the biological mechanisms are, it is possible to imagine what goes on. Once opened, the distal extremity cannot close itself, leaks some of its protoplasm and—whatever the reason is—cannot control its ionic equilibrium.

So, even if the upper end is opened again, the deflation and the ionic disturbance of the lower end will render difficult the passage of the nervous impulse, and then will eventually make it impossible as time goes by.

The second rule of cellular surgery is that it is an emergency type of surgery. It is urgent to stop the metabolic degradation of the distal nerve end. Here again, cold seems to be the best solution. While there is no real hurry as far as the proximal end is concerned the distal end of an injured nerve should be attended to immediately and cooled down as soon as possible, even before the treatment of any other associated injury.

If it has been possible to stop in due time the degradation of the lower end—i.e. the "protoplasmorrage"—or if it has been possible to reinflate that lower end by any artificial means, it should be sufficient to "open" again the proximal portion and to approximate and align the two ends in order to convey the nervous impulse. Hopefully the healing of the membrane will then splice the lower end onto the upper end of the axon, thus resulting in a quick or maybe even instant cellular repair or fusion, without the help of any suture, stitches or other artificial means, and thereby preventing the Wallerian degeneration.

The third rule of cellular surgery is evidently to overcome the normal tension which tends to pull apart the segments, retracting them in a significant and importunate manner. The most inadequate way to do so is to suture the envelopes of the axonal bunches which results in "pulling the nerve by its sleeve" while it should be "pushed forward from the back". In all cases conventional suturing, however fine and microscopic, of any external envelope or internal sheets of the nerve must always be condemned to failure, because of the inevitable retroaction of the axons inside their "sleeves", i.e. their envelopes.

As is more fully detailed below, the present invention employs these rules of cellular surgery by gently seizing and clamping each severed nerve end in a circular holding chamber, molding the nerve into a circular cross section. The chamber incorporates holding means, preferably a partial vacuum acting laterally on the nerve end and not endwise, presenting the nerve end without withdrawal ready for trimming. The chamber also provides cooling means to retard Wallerian degeneration, temperature monitoring means, and electrical stimulation means to provide mild continuous stimulation of the nerve during the holding operation. The preferred circular cross section facilitates the shaping of both nerve ends into matching shapes, permitting rapid comparison and angular rotation into mating alignment for optimum reconnection of individual nerve fibers.

The invention is applicable to any nerve or bundles of nerves in the human body, including the spinal cord. The only variation that needs to be made for different nerves of definite shape is the use of a chamber which best approximates the normal size and shape of the nerve to be repaired. Although a circular holding chamber having the appropriate diameter is believed to best approximate the shape of most nerves, other configurations may be employed without departing from the scope of this invention.

By referring to FIG. 1, the overall method and apparatus of the present invention can best be understood. As shown therein, a suitable surgical clamp member 20 is shown with a chamber 22 securely engaged in one jaw 26 of clamp 20 and a chamber 23 securely engaged in the other jaw 27 of clamp 20. As is readily apparent to one of ordinary skill in the art, clamp 20 is merely shown for illustrative purposes, with any other holding apparatus meeting the criteria which will be detailed below being equally applicable and useful in carrying out the present invention.

As depicted in FIG. 1, the proximal end 24 of the severed nerve is peripherally surrounded and held by chamber 22 while the distal end 25 of the severed nerve is peripherally surrounded and held by chamber 23. In the embodiment depicted in FIG. 1, jaw 27 is constructed to allow chamber 23 to be rotated about its central axis in order to maximize the reattachment of identical fascicles and axons. The actual method and apparatus for achieving this rotational alignment is detailed below. Although this embodiment depicts jaw 27 as allowing the rotation of chamber 23, it is certainly within the purvue of the present invention for jaw 26 to be the sole rotational jaw or for both jaws 26 and 27 to provide the desired rotation.

CHAMBER CONSTRUCTION

Figure 2:
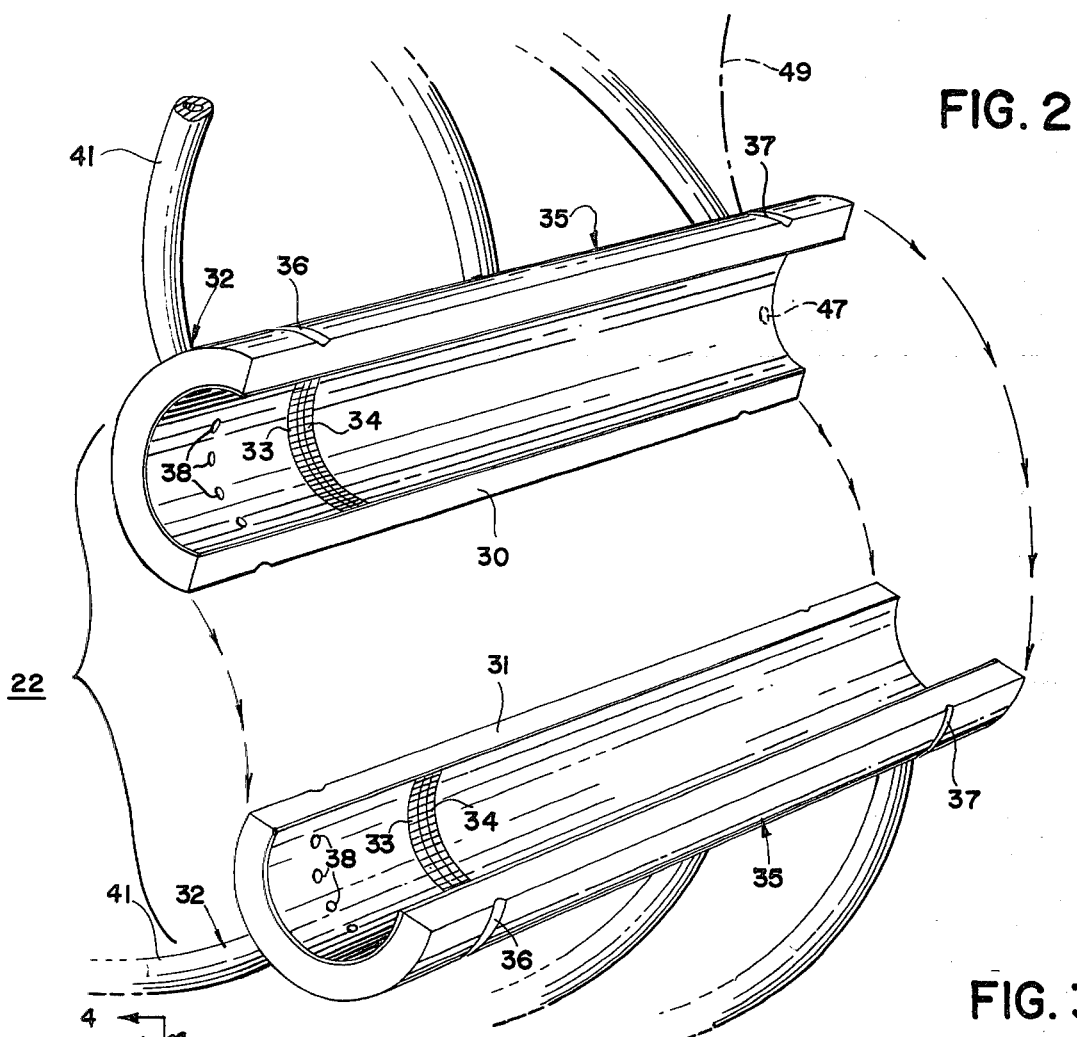
FIG. 2 is a perspective view of one of the nerve holding chambers of the present invention shown greatly enlarged in its open position.

In FIG. 2, the preferred embodiment of a nerve holding chamber of the present invention is shown. As depicted therein, holding chamber 22 comprises an overall cylindrical shape formed of two substantially identical portions 30 and 31. With this construction, a nerve can be easily positioned within one of the two portions and then peripherally surrounded and enclosed within both mating portions in a manner which assures complete embraced gripping of the nerve, while also allowing quick and easy removal of chamber 22 when the procedure has been completed.

Both portions 30 and 31 incorporate along its axial length nerve holding means 32 at one end thereof, electrodes 33 and 34, and a cooling jacket 35. In addition, portions 30 and 31 also incorporate external annular grooves or notches 36 and 37 formed in the outer peripheral surface thereof to accommodate suturing or other fastening means. In whis way, chambers 30 and 31 are easily maintained in juxtaposed peripherally embracing relationship with the nerve contained therein.

Figure 3:
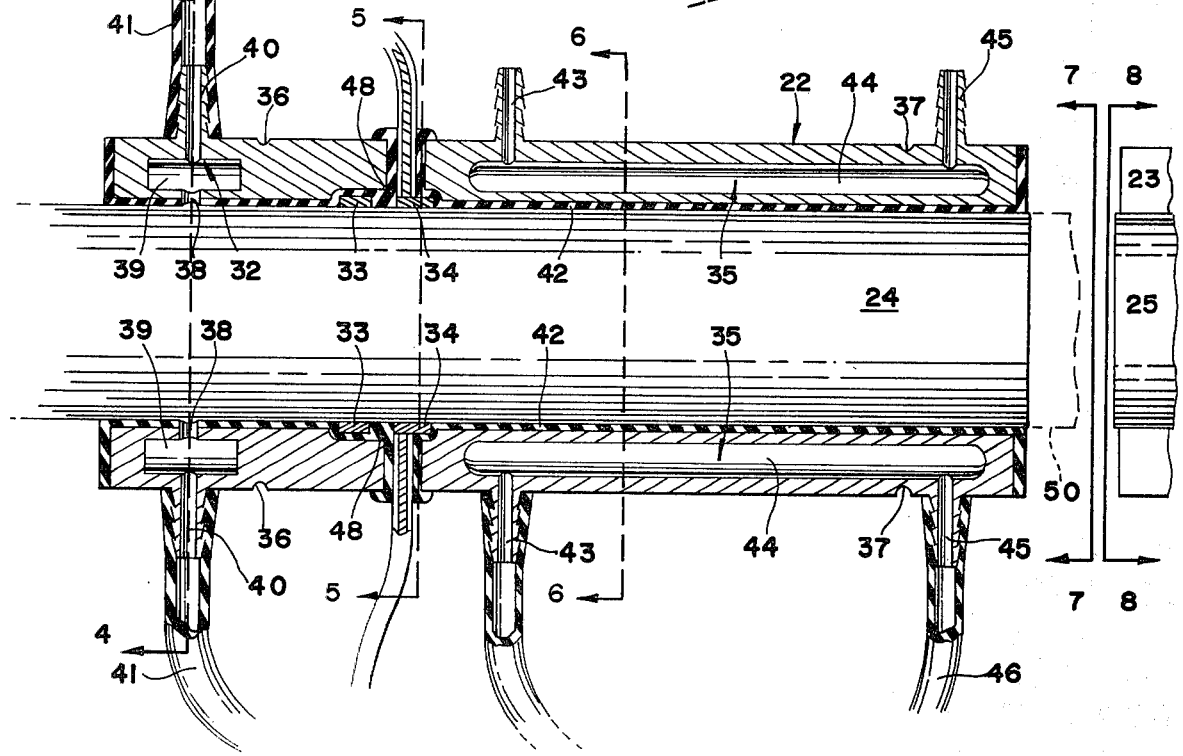
FIG. 3 is a cross sectional side elevation view taken along the central axis of the nerve holding chamber of the present invention in a closed position peripherally encircling and holding a portion of a severed nerve.

As shown in FIG. 3, nerve 24 is peripherally embraced within chamber 22, ready for reattachment and repair. It is important to note in FIGS. 2, 3 and 4 that nerve holding means 32 must be positioned at the opposed end from the severed end of nerve 24. In this way, both the epineurium, fascicles, and axons contained within the nerve are fully embraced, preventing retreat of the fascicles from the open end. By embracing and holding nerve 24 at a position removed from the severed proximal end of nerve 24, nerve 24 can be moved into juxtaposed contacting relationship with the severed end of the distal portion 25 of the nerve without experiencing any undesirable protoplasma loss or retreat of the fascicles from the severed ends.

In the embodiment depicted in FIGS. 2, 3, and 4, holding means 32 comprises a vacuum system which assures secure holding engagement of the nerve in the desired remote position. In this embodiment, sections 30 and 31 both incorporate a plurality of apertures 38 which communicate with a plenum 39 formed within each section. Each of the plenums 39 communicate with portals 40 to which are attached vacuum lines 41 in order to provide the requisite pressure differential to assure that nerve 24 is securely held in position.

As is more fully described below, the reattachment and repair of the nerve is effectuated by imparting electrical stimulation to the nerve once the precise position for reattachment has been determined and the nerves have been placed in contacting juxtaposition. In order to provide this electrical stimulation as well as to assure receipt of electrical impulses, chamber 22 incorporates electrodes 33 and 34 peripherially surrounding the inner wall of both sections 30 and 31, as shown in FIGS. 2, 3 and 5. In the preferred embodiment, two isolated electrodes are employed and are positioned to be certain that an electrical impulse is transmitted downstream from the proximal end towards the distal end of the nerve. Preferably, electrodes 33 and 34 are positioned adjacent to each other and spaced about 1-5 millimeters. In addition, each electrode is isolated from each other by employing a nonconductive member 48 about each electrode.

In the preferred embodiment, the electrodes contained in chamber 23 are employed to receive the impulses passing through the nerve. However, if desired, receiving electrodes can be placed on the nerve along the distal portion at a position downstream from chamber 23.

As best seen in FIGS. 3 and 4, the entire internal surface of chamber 22 incorporates a nonconductive surface 42 in order to prevent any undesirable or unwanted electrical stimulation. In this way, only electrodes 33 and 34 can impart electrical stimulation to the nerve contained within the chamber of this invention.

As shown in FIGS. 3 and 6, chamber 22 also preferably incorporates a separate cooling system 35 formed in each of the portions 30 and 31. As has been discussed above, the cooling of the nerve is important in order to reduce the cellular metabolism, without causing damage to the nerve. As a result, chamber 22 preferably incorporates an inlet portal 43, a cooling zone 44 through which the cooling fluid flows and an exit portal 45. Of course, appropriate tubing 46 is mounted to portals 43 and 45 to assure the free flow of the cooling fluid into and out of cooling zone 44 of chamber 22.

Although various cooling fluids can be employed to reduce the cellular metabolism of the nerve without damaging the nerve, it has been found that moderate cold water ranging between 4° C. and 9° C. provides the desired results.

An additional optional feature that can be incorporated into chamber 22 is a thermocouple 47, shown in FIG. 2 in phantom. Thermocouple 47 with its lead 49 can be mounted directly to the end of chamber 22 in order to have the temperature of the nerve endings easily determinable whenever required. In this way, the proper cooling can be precisely regulated in order to prevent nerve damage while also reducing the nerves' natural metabolism. If desired, thermocouple 47 and lead 49 can be mounted in various other positions, as well as being controlling connected to the cooling fluid system for automatically varying the cooling flow to achieve the optimum temperature.

Although the nerve holding chamber described above details the preferred embodiment of the chamber of the present invention for mounting to the proximal end of the nerve, it will be readily apparent to one skilled in the art that the chamber mounted to the distal end of the severed nerve is a substantially identical, mirror image thereof. In addition, variations can be made in the structure discussed above without departing from the scope of this invention. Consequently, any such variations which employ the teaching of this invention do not depart from the scope of the present invention and are included herein.

METHOD OF REPAIR

In order to properly reattach and repair a severed nerve, it is important to remember that the distal end of the severed nerve degenerates if left alone. Since the distal end of the nerve is unable to form a closing membrane, as occurs with the proximal end, the distal end leaks its protoplasm and is unable to control its ionic equilibrium. In order to stop or retard this metabolic degradation, it has been found to be extremely important to cool the severed distal nerve end as quickly as possible. This can be done in a variety of ways, including securing one of the chambers of the present invention to the distal end and running the coolant through the jacket in order to maintain the distal end in the cooled state until operative surgery is ready to be performed.

Prior to commencing the actual nerve reattachment, the distal end of the severed nerve is placed in chamber 23, if this has not already been done in order to maintain the distal end in a cooled state. Then, the proximal end of the severed nerve is placed in chamber 22. The nerve securing means 32 of both chambers 22 and 23 are applied to the nerve while the cooling system 35 of both chambers is similarly operated to cool the nerve. Similarly, chamber portions 30 and 31 are secured in peripheral holding contact, with the nerve contained therein, with portions 30 and 31 maintained in abutting contact by applying sutures to recesses 36 and 37.

Once proximal end 24 of the nerve is secured in chamber 22 and distal end 25 of the nerve is secured in chamber 23, both chambers 22 and 23 are securely clamped in appropriate holding clamp means such as the clamp 20 depicted in FIG. 1.

With the proximal and the distal end of the severed nerve positioned and securely held in the chambers of the present invention, the surgical process for reattachment and repairing the severed nerve may commence. As previously discussed, the proximal end of the severed nerve closes itself by solidifying its protoplasm and building up a new membrane from this protoplasm. As a result, portion 50, shown in phantom in FIG. 3, must be cut off from the proximal portion 24 of the nerve prior to effectuating the nerve repair. This removal can be achieved using a variety of well-known surgical implements such as scalpels or surgical scissors.

Once the proximal end 24 of the nerve has been reopened, the plurality of fascicles forming the nerve and exposed at the open ends of both the proximal and distal ends are viewed to determine the optimum orientation of the nerve for reattachment. By referring to FIGS. 7-10, this reorientation process for optimum positioning using the present invention can best be understood.

In FIGS. 7 and 9, the end of chamber 22 is shown with a plurality of indicia scaled about the end surface. In addition, the epineurium 52 of proximal end 24 of the nerve is shown along with the plurality of fascicles 53 peripherally enveloped by epineurium 52.

Similarly, as shown in FIGS. 8 and 10, chamber 23 incorporates indicia scaled about the end thereof while also exhibiting the plurality of fascicles 53 and epineurium 52 viewable on the transected distal end 25 of the severed nerve. Upon viewing the fascicles as represented by FIGS. 7 and 8, in reference to the indicia markings on the outer edges of chambers 22 and 23, it can be observed that one of the fascicle portions in nerve end 24 lying along the marking of about 19° is substantially identical to the fascicle positioned at 110° of chamber 23 in nerve end 25.

As a result, chamber 23 is arcuately rotated until the 110° marking on chamber 23 is in a position which will bring it into direct alignment with the 19° marking on chamber 22. When these two positions are aligned and chambers 22 and 23 are brought into facing juxtaposition and contact with each other, the fascicles 53 of the nerve are positioned for maximum identical reattachment.

I have found that to achieve the repair of most types of severed nerves with a maximum of identical fascicle reattachment, a chamber which is substantially circular in cross-section is best to employ. By using circular chambers, the plurality of fascicles of the nerve in both ends are forced into a more circular pattern. In this way, irregular or unconsistant configurations in the two ends are reduced and matching contact of identical, aligned fascicles is maximized. Although some nerves, such as the spinal nerve, may require a special shaped chamber for optimum results, the circular chambers are preferred for repairing most severed nerves.

In order to best maximize the alignment of identical fascicles prior to the repair of the nerve, micro-surgery techniques should be employed, and an optical system which will simultaneously view both the distal end and the proximal is most desirable. In this way, the simultaneous viewing of both ends will allow rotation of one or both of the chambers until the best position for reattachment is achieved.

It is also possible to use the teaching of the present invention along with computer analysis of the optical images of the proximal and distal ends of the nerve so that reattachment of identical fascicles aligned beyond the perception limits of the human eye can be realized.

Once chambers 22 and 23 have been rotated into the optimum position for reattachment, chambers 22 and 23 are brought into abutting endurse contact with each other by employing clamping means 20. As has been described above, the movement of chambers 22 and 23 with its secure holding of the nerve at a position remote from the severed ends of the nerve assures that the nerve ends are presented without any detrimental retreat of the fascicles from the open end. As a result, when chambers 22 and 23 are brought into juxtaposed, facing contact with each other, the fascicles contained in the proximal end and the fascicles contained in the distal end are placed into abutting contact.

The reattachment process is then completed by applying an electrical impulse through contacts 33 and 34 in order to force an electrical pulse signal from the proximal end towards the distal end. By employing contacts 33 and 34 of chamber 23, a pulse signal is generated which is directed downstream towards the distal end. Signal receiving electrodes are mounted to the distal end in order to provide positive receiving means to confirm the passage of the electrical impulse through the severed end.

I have found that by employing this process, immediate restoration of physical and electrical activity is obtained with the electrical signal being transmitted from the proximal nerve end through the previously severed section to the electrode contained in the chamber 23 on the distal nerve end. In order to assure recording of only electrical conductivity passing through the nerve, the electrical recording means mounted on the distal end of the nerve is preferably positioned about 2-3 centimeters away from the electrodes of the proximal portion. Preferably, the electrodes of chamber 23 are used for recording, but separate signal receiving means can be mounted directly to the distal portion of the nerve if so desired.

In order to effectuate the complete reattachment and repair of the severed nerve, electrical conductivity is maintained in the nerve with chambers 22 and 23 being maintained in contacting juxtaposition throughout this period. Although the length of time required varies depending upon the size and location of the nerve and the electrical stimulation being applied, it has generally been found that a period of about 5 hours is sufficient to complete this self healing repair. After this period of time, chambers 22 and 23 are delicately removed.

Upon removal, it is observed that the nerve looks optically healed without the help of any sutures or other type of fastening means. However, since the mechanical solidity of the repair is not complete at this time, the nerve should only be moved softly in order to prevent breakage.

It will thus be seen that the objects set forth above, among those made apparent from the preceding description, are efficiently attained and, since certain changes may be made in carrying out the above method and in the construction set forth without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described my invention, what I claim is new and desire to secure by Letters Patent is:

1. A method for reattaching and repairing severed nerves comprising the steps of
    A. cooling the distal portion of the severed nerve as quickly as possible to retard degradation thereof;
    B. embracing the distal portion of the severed nerve in a distal nerve holding chamber;
    C. securing the distal portion of the severed nerve to the distal nerve holding chamber at the end of the chamber opposed from the severed end of the nerve;
    D. embracing the proximal portion of the severed nerve in a proximal nerve holding chamber;
    E. securing the proximal portion of the nerve to the proximal nerve holding chamber at the end of the chamber opposed from the severed end of the nerve;
    F. trimming the proximal end of the severed nerve to remove any closure thereof;
    G. viewing the proximal end and the distal end of the severed nerve to determine the pattern of fascicles contained therein;
    H. rotating one of the holding chambers to align fascicles in the proximal portion of the severed nerve with the corresponding fascicles of the distal portion of the severed nerve;

I. moving the proximal portion and the distal portion of the severed nerve into abutting juxtaposed contacting relationship with each other; and J. applying electrical impulses to the proximal portion of the severed nerve directed for transmission to the distal portion of the severed nerve.

2. The method defined in claim 1, and comprising the additional step of

K. monitoring the electrical impulses generated at the proximal portion of the severed nerve along the distal portion of the severed nerve.

3. The method defined in claim 1 wherein the securement of the severed nerve portions to the chamber is achieved by applying vacuum gripping means to the portions of the severed nerve.

4. Apparatus for use in reattaching severed nerves comprising

A. a nerve holding member removably securable about each of the ends of a severed nerve;

B. securing means cooperatively associated with the nerve holding members for securing both portions of the severed nerve at a position removed from the severed nerve ends;

C. means for moving the severed nerve ends into juxtaposed facing contacting relationship; and D. rotation means for altering the relative circumferential position of the nerve holding member in a manner which will substantially align the fascicles of the proximal portion of the severed nerve with the corresponding fascicles of the distal portion of the severed nerve, thereby providing reattachment and repair of a maximum number of nerve fascicles, whereby a severed nerve is securely held and movable without detrimental effects thereto while also being able to be brought into juxtaposed contacting relationship for reattachment and repair.

5. The apparatus defined in claim 4, wherein said nerve holding members are further defined as comprising index means formed on the ends thereof for providing readily viewable reference locations between the fascicles of the severed nerve and the chamber itself.

6. The apparatus defined in claim 5 further comprising magnifying means for viewing the ends of the severed nerve and aligning corresponding fascicles of the severed nerve ends with each other.

* * * * *